United States Patent [19]

Monte

[11] Patent Number: 4,931,300

[45] Date of Patent: Jun. 5, 1990

[54] ANTIMICROBIAL FOOD COMPOSITION

[75] Inventor: Woodrow C. Monte, Tempe, Ariz.

[73] Assignee: Doyle W. Boatwright, Phoenix, Ariz.; a part interest

[21] Appl. No.: 294,642

[22] Filed: Jan. 9, 1989

[51] Int. Cl.$^5$ ................................................ A23L 3/34
[52] U.S. Cl. .................................... 426/335; 426/532; 426/656; 426/658
[58] Field of Search ............... 426/532, 331, 335, 658, 426/656

[56] References Cited

U.S. PATENT DOCUMENTS 4,081,555 3/1978 Sawhill ............................... 426/532
4,112,123 9/1978 Roberts ................................ 426/74

Primary Examiner—R. B. Penland
Attorney, Agent, or Firm—Tod R. Nissle

[57] ABSTRACT

A nutritionally balanced water soluble powdered food composition which, when mixed with water, has a low pH, extended shelf life, high antimicrobial activity, and which includes protein alpha-amino acids in solution or in suspension.

3 Claims, No Drawings

ANTIMICROBIAL FOOD COMPOSITION

This invention relates to nutritionally balanced food compositions for ingestion along the digestive tract of a patient.

More particularly, the invention relates to nutritionally balanced water soluble powdered food compositions which, when mixed with water, have a low pH, extended shelf life, high antimicrobial activity, and which include protein alpha-amino acids in solution or in suspension.

Water soluble powdered nutritionally balanced food compositions are known in the art. See, for example, U.S. Pat. No. 4,112,123 to Roberts. The Roberts patent discloses a nutritionally balanced powdered water soluble food composition. The Roberts food composition has a pH in the range of 3.0 to 8.0, preferably 6.5 to 7.0. The food composition described in the Roberts patent has several potential disadvantages. Protein tends to precipitate from solutions which, like the Roberts food composition, have acidic pH values in the range of 2.0 to 5.5. Solutions with low pH values in the range of 2.0 to 5.5 are, however, often preferred because the acidity of the solutions normally, as a rule, provides a high level of antimicrobial activity. Food compositions like the compositions disclosed in the Roberts patent are an exception to this rule and do not provide a high antimicrobial activity. This is evidenced by the fact that the Roberts food composition must be refrigerated after it is reconstituted and must then be utilized within about twenty four hours.

Accordingly, it would be highly desirable to provide a water soluble food composition which would, when mixed with a liquid, form a solution which has a pH in the range of 2.0 to 5.5, has a high antimicrobial activity, has an extended shelf life, and which prevents protein alpha-amino acids from precipitating from solution.

Therefore, it is a principal object of the invention to provide an improved food composition.

Another object of the invention is to provide a nutritionally balanced liquid soluble food composition including protein alpha-amino acids which, when reconstituted in aqueous solution at a pH of 2.0 to 5.5, generally prevents the protein amino acids from precipitating or separating from the aqueous solution.

A further object of the invention is to provide a nutritionally balanced water soluble food composition which, when reconstituted in an aqueous solution, has a high antimicrobial activity and has an extended shelf life.

These and other, further and more specific objects and advantages of the invention will be apparent to those skilled in the art from the following detailed description thereof.

.Briefly, I have discovered a food composition which has a high antimicrobial activity and extended shelf life. The food composition includes from 6% to 28% by weight of water soluble protein alpha-amino acids; from 4 to 22% by weight of triglycerides of predominantly 6 to 26 carbon atoms in the fatty acid chain; from 45% to 75% by weight of carbohydrates selected from the group consisting of corn syrup solids, trisaccharides, tetrasaccharides, pentasaccharides, hexasaccharides, dextrose, fructose, sucrose, maltose, oligosaccharides and high saccharides; from 0.1% to 6% by weight of an emulsifier; from 0.1% to 6% by weight of an edible acid; and, from 0.05% to 6.0% by weight of an antimicrobial agent selected from the group consisting of sorbic acid, benzoic acid, sodium benzoate, potassium sorbate, sodium sorbate, and potassium benzoate. The food composition provides up to about three calories per cubic centimeter of composition. On being reconstituted with a liquid, the composition forms a liquid solution which has an osmolarity of 250 to 650 and in which at least twenty one percent by weight of the acid formed in the liquid solution by the antimicrobial agent is undissociated acid. The pH of the reconstituted food composition is from 2.0 to 5.5.

For purposes of the present specification, the term protein alpha-amino acids is defined to include monopeptides, dipeptides, tripeptides, and oligopeptides prepared by the partial hydrolysis of proteins or by synthesis and to include whey protein.

Peptide alpha-amino acids are preferred in the practice of the invention because they help tremendously in reducing the pH of the food composition and, consequently, in reducing the quantity of acidulant required in preparing the food composition. A peptide is any of a class of amides that are derived from two or more amino acids by combination of the amino group of one acid with carboxyl group of another, that yield these acids on hydrolysis, that are classified according to the number of component amino acids, and that are obtained by partial hydrolysis of proteins or by synthesis (as from alpha-amino acids or their derivatives). A dipeptide is a peptide that yields two molecules of amino acid on hydrolysis. A polypeptide is a polyamide that yields amino acids on hydrolysis but has a lower molecular weight than a protein and that is obtained by partial hydrolysis of proteins or by synthesis. Peptides are easier to digest than whey and other proteins.

Peptides are prepared from hydrolyzing proteins of any kind, and are commonly prepared by hydrolyzing egg, milk, or soy.

For purposes of the present specification, the term "whey protein" is defined to mean that water soluble or suspendible, essentially undenatured protein fraction derived from cheese whey which protein fraction is, essentially, retained by an ultra-filtration membrane that permits lactose, lactic acid, and soluble salts to pass through the membrane Whey protein is specific and identifiable in terms of its composition and is not, necessarily, depend upon a process for production thereof. Whey protein may be obtained by methods other than ultra--filtration, e.g., gel filtration.

The amount of protein alpha-amino acids used in the present composition may vary widely, but for most applications from 6% to 22% on a dry weight basis is suitable, especially between about 15% and 20%.

The protein alpha-amino acids are essentially water soluble or suspendible, and capable of being compounded or formulated into stable and pourable form in order to function in the manner required. Further, it is the protein alphaamino acid fraction containing one or more of the more than twenty alpha-amino acids, most of which have the general formula RCH(NH$_2$)COOH, that are synthesized in plant and animal tissues, that are considered the building blocks of proteins, from which they can be obtained by hydrolysis, and that play an important role in metabolism, growth, maintenance and repair of tissue.

Table 1 in U.S. Pat. No. 4,112,123 to Roberts shows a typical amino acid profile for whey protein used in the present invention.

Medium-chain triglycerides (MCT's) utilized in the food composition of the invention produce a composition of low viscosity while concommittently providing high caloric content and easily digestible compositions. The fatty acid chains of the medium-chain triglycerides are predominantly between about 6 and 12 carbon atoms, and are preferably utilized in conjunction with long-chain triglycerides (LCT's) in which the fatty acid chains are predominately between about 14 to 26 carbon atoms.

The proportion of LCT's and MCT's in the food composition can vary widely, but typically is about 4% to 22% by weight, with 12%—18% being an optimal range.

Any food grade emulsifier is used for present emulsification purposes and combinations of emulsifiers are used if desired. Any of the long fatty acid glycerol emulsifiers can be used, which normally have a C-12 to C-20 esterified chain. Typical among these are glycerollactopalmitate or the sterate. Alternatively, propolyene derived emulsifiers may be used, such as prophylene glycomonosterate, or the oleate, palmitate, and myristate. Likewise, the "Span" series of emulsifiers may be used. These are well-known emulsifiers and are fatty acid partial esters of the sorbitol anhydrides (or sorbitan). One well known emulsifier is the "Tween" series of polyoxyethylene derivatives of fatty acid partial esters of sorbitol anyhdride. Tween 80 and Atmos 300 are often used in combination. The well known Atmos series of mono and diglycerides may be used. Also, lecithin is a suitable emulsifier. The amount of the emulsifier is chosen to suit the particular composition, and generally ranges from about 0.1% to 6.0% by weight.

The food composition contains from 45% to 75% by weight of carbohydrates. The carbohydrates may be any of the digestible carbohydrates such as dextrose, fructose, sucrose, maltose, oligsaccharides, higher saccharides, or mixtures thereof, depending on usage.

Vitamins, minerals, an other trace elements can be used to supplement the food composition and for purposes of total nutritional balance. These supplements can be varied as desired but are typically equal to the RDA or greater based on 2,000 calories. Soy bran, rice bran or other fiber polysaccharides or sources of fiber can be included in the food composition.

Conventional coloring agents, such as the USDA colors, may be used, as well as conventional preservatives, such as BHT and BHA. BHT and BHA preserve fats.

The food composition is provided in a powdered form having a relatively low moisture content. The moisture content is, as is the case for many powdered formulations, preferably at least below 4% by weight and more preferably below 3% by weight. Such low moisture content provides a product having a shelf life of at least one year shelfstability at ambient conditions if hermetically sealed.

The powdered form of the food composition may be reconstituted with a liquid. The liquid form of the food composition of the invention need not be pasteurized or stored under refrigerated conditions.

The dried powder is reconstituted with any desired edible liquid. The powder is ordinarily partially dissolved and partially suspended in the resulting liquid form of the invention. While it is possible to reconstitute the composition with liquid such as alcohol, the reconstituting liquid will ordinarily be principally water. The water may contain additional ingredients such as alcohol, glycerol, proplyene glycol, sugars, and flavor.

The caloric content of liquid solutions of the reconstituted food composition of the invention is adjusted to any desired level up to about 3 calories per cubic centimeter. One half to two calories per cubic centimeter is preferred.

The osmolarity of the reconstituted food composition is in the range of 250 to 650, but preferably is in the range of 275 to 350 mOSm per liter of 1 calorie per cubic centimeter of food.

The food compositions also include edible acidulants such as malic acid, acetic acid, citric acid, lactic acid, sodium acetate, fumeric acid, or an acidic salt such as sodium acetate in order to adjust the pH within the range of 2.0 to 5.5. This pH range is critical to the extended shelf life of the invention. Any pH in excess of about 5.5 is not preferred because such allows greater microbial activity and minimizes the antimicrobial effects of sorbates and benzoates utilized in the invention. A pH greater than 6.0 is totally unacceptable because of the greatly reduced antimicrobial activity of the sorbates and benzoates critical to the invention.

The antimicrobial activity of sorbic and benzoic acid is due primarily to the undissociated acid molecule. Antimicorbial activity is therefore pH dependent and the estimated activity at any pH can be estimated as shown below in Table 1.

TABLE 1
EFFECT OF pH ON DISSOCIATION

| pH | Percent Undissociated Acid | |
|---|---|---|
|  | Sorbic | Benzoic |
| 3 | 98 | 94 |
| 4 | 86 | 60 |
| 5 | 37 | 13 |
| 6 | 6 | 1.5 |
| 7 | 0.6 | 0.15 |

The food composition includes a sorbate or benzoate such as sorbic acid, benzoic acid, potassium sorbate, sodium sorbate, potassium benzoate, sodium benzoate, and the like. Such benzoates and sorbates are crucial because at low pH values in the range of 2.0 to 5.5 they provide significant antimicrobial activity. Further, the sorbate and benzoate antimicrobial agents are important because there are, apart from the sorbates and benzoates I discovered in the invention, apparently no other comparable antimicrobial agents that will function in conjunction with protein alphaamino acids. The combination of protein alpha-amino acids and a benzoate and/or sorbate at a pH in the range of 2.0 to 5.5 overcomes this problems and produces a food composition having an extended shelf life after being reconstituted with water or another liquid. The food composition of the invention also prevents the separation or precipitation of the suspended or dissolved protein alpha-amino acids in reconstituted liquid solutions of the food composition.

After the dried powder food composition of the invention is reconstituted and refrigerated, it has an extended shelf life of about seventy-two (72) hours or more. The ratio of water to composition will vary with the proportion of the ingredients of the composition and with the desired consistency required, as discussed above. By way of example, on a weight/weight basis of composition to water, the dilutions on a 100 gram basis can be:

| Calories/ml. of solution | To make 100 grams solution gms powd*/gms water |
| --- | --- |
| .5 | 18/82 |
| 1 | 25/75 |
| 1.5 | 32/68 |
| 2.0 | 40/60 |

*Powder of Example 1 below.

The following examples depict the presently preferred embodiments of the invention for the purpose of illustrating the practice thereof and not by way of limitation of the scope of the invention. In the examples, all proportions are by weight, unless otherwise noted.

EXAMPLE 1

The food composition in powder form is prepared by blending a number of ingredients.

| | |
| --- | --- |
| MOLTODEXTRAN (POLYSACCHARIDE) | 27.85536 |
| MALTODEXTRAN AGGLOMERATED | 24.53924 |
| MCT OIL | 6.76487 |
| CORN OIL | 6.76487 |
| WHEY PROTEIN POWDER | 9.28512 |
| HYDROLYZED PROTEIN POWDER (dipeptides, tripeptides, oligopeptides) | 8.84297 |
| SODIUM ACETATE | 0.88430 |
| POTASSIUM CITRATE | 0.57479 |
| VITAMIN D3 (1000,000 IU/GM) | 0.00292 |
| CYANOCOBALAMIN (0.1%) | 0.00575 |
| SODIUM SORBATE | 1.59173 |
| SOY POLYSACCHARIDE (FIBER) | 7.29545 |
| TOTAL WEIGHT | 100.00000 |

The approximate percent Calories from the various ingredients are carbohydrates 52.4%, fat 30.5%, and protein 17.1%. The carbohydrates included in the powder food composition include sucrose, dextrose, maltose, lactose, trisaccharides, tetrasaccharides, pentasaccharides, hexasaccharides, and higher saccharides. The food powder composition has a caloric density (Cal/ml) of 1.07; of total Cal/Nitrogen ratio of 145.9; a non-protein Cal/Nitgrogen ratio of 120.9; a protein concentration of 45.8 g/liter; a fat concentration of 36.1 g/liter; a carboydrate (digestible) concentration of 140.0 g/liter; a carboydrate (total) concentration of 153.8 g/liter; and a dietary fiber concentration of 14.0 g/liter.

During the blending of the above-listed ingredients of the food composition, agglomeration techniques are preferably employed to make the resulting powder mixture more easily dispersed and soluble in water.

EXAMPLE 2

Twenty-five grams of the food composition powder of Example 1 is mixed with 75 grams of water. The resulting drink provides 1.1, calories per cubic centimeter, has a pH of 4.7, and has an osmolarity of 300.

EXAMPLE 3

The powder of Example 1 is prepared, except 9.28512 grams of polypeptide hydrolyzed protein powder is substituted for the 9.28512 grams of whey protein powder. Similar results are obtained.

EXAMPLE 4

Twenty-five grams of the food composition powder of Example 3 is mixed with 75 grams of water. The resulting drink provides 1.1 calories per cubic centimeter, has a pH of about 4.5, and has an osmolarity of about 350.

EXAMPLE 5

The powder of Example 1 is prepared, except 1.59173 grams of potassium benzoate is substituted for the 1.59173 grams of sodium sorbate.

EXAMPLE 6

Twenty-five grams of the food composition powder of Example 5 is mixed with 75 grams of water. The resulting drink provides 1.1 calories per cubic centimeter, has a pH of about 4.5, and has an osmolarity of about 350.

EXAMPLE 7

Thirty grams of the food composition powder of Example 1 is mixed with 45 grams of water. The mixture is brought to a simmer in a pan with stirring and cooled in a refrigerator to produce a curdled dessert.

EXAMPLE 8

Thirty grams of the food composition powder of Example 1 is mixed with 3 grams of water and rolled in sucrose powder. The rolled mixture is coated with chocolate or some other desired candy coating.

EXAMPLE 9

Seventy five grams of the food composition powder of Example 1 is combined with 63 grams of water and 1.1 grams of gelatin, as follows. The gelatin is dissolved in 135° F water and the powder is then added. The mixture is thoroughly mixed and cooled in a refrigerator for 1.5 hours.

The food composition of the invention is ingested at any desired point along the digestive tract, but ordinarily is administered to a patient orally or is tubally fed directly into the patient's stomach. If appropriate, the reconstituted food composition can be tubally directly fed into the intestinal tract or the esophagus.

Having described my invention in such terms as to enable those skilled in the art to understand and practice it, and having identified the presently preferred embodiments thereof,

I claim:

1. A food composition for ingestion along the digestive tract of a patient, said food composition consisting of:
    (a) from 6% to 28% by weight of water soluble peptide alpha-amino acids, said peptide alpha-amino acids lowering the pH of an aqueous solution of said food composition;
    (b) from 4% to 22% by weight of triglycerides of predominantly 6 to 26 carbon atoms in the fatty acid chain;
    (c) from 56% to 75% by weight of carbohydrates selected from the group consisting of corn syrup solids, trisaccharides, tetrasaccharides, pentasaccharides, hexasaccharides, dextrose, fructose, sucrose, maltose, oligosaccharides and higher saccharides;
    (d) from 0.1% to 6.0% by weight of an emulsifier;
    (e) from 0.1% to 6.0% by weight of an edible acid for adjusting the pH of the food composition within the range of 2.0 to 5.5;
    (f) from 0.5% to 6.0% by weight of an antimicrobial agent selected from the group consisting of sorbic acid, benzoic acid, sodium benzoate, potassium sorbate, sodium sorbate, and potassium benzoate.

2. The food composition of claim 1 in liquid form and
(a) including water;
(b) providing from 0.4 up to about 3 calories per cubic centimeter of composition;
(c) including at least 21% by weight of the acid formed in said composition by said antimicrobial agent as undissociated acid.

3. The food composition of claim 1 in the form of an aqueous solution having an osmolarity in the range of 250 up to about 375.

* * * * *